United States Patent [19]

Ishikawa et al.

[11] Patent Number: 5,380,921

[45] Date of Patent: Jan. 10, 1995

[54] AMINOPHOSPONIC ACID DERIVATIVE

[75] Inventors: Kiyofumi Ishikawa; Takehiro Fukami; Takashi Hayama; Kenji Matsuyama; Kazuhito Noguchi; Mitsuo Yano, all of Tokyo, Japan

[73] Assignee: Banyu Pharmaceutical Co., Ltd., Tokyo, Japan

[21] Appl. No.: 55,872

[22] Filed: May 4, 1993

[51] Int. Cl.$^6$ .............................................. C07F 9/08
[52] U.S. Cl. ...................................... 562/16; 562/17
[58] Field of Search ........................................ 562/16, 17

[56] References Cited

FOREIGN PATENT DOCUMENTS 0103867  3/1984  European Pat. Off. .
0401963  12/1990 European Pat. Off. .
0511940  11/1992 European Pat. Off. .
1160992  6/1989  Japan .

OTHER PUBLICATIONS

Flynn et al, "The Synthesis of an Aminophosphonic Acid Converting Enzyme Inhibitor", *Tetrahedron Letters*, 27:1757–1758 (1986).
Bertenshaw et al, "Phosphorus–Containing Inhibitors of Endothelin Converting Enzyme; Effects of the Electronic Nature of Phosphorus on Inhibitor Potency", *J. Med. Chem.*, 36:173–176 (1993).
Okada et al, *Biochem. Biophys. Res. Commun.*, 171(3):1192–1198 (1990).

*Primary Examiner*—José G. Dees
*Assistant Examiner*—Joseph M. Conrad, III
*Attorney, Agent, or Firm*—Sughrue, Mion, Zinn, Macpeak & Seas

[57] ABSTRACT

There are provided novel aminophosphonic acid derivatives of the general formula [I]:

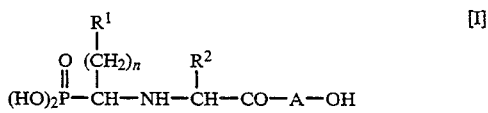

wherein n is an integer of 2 or 3; $R^1$ is a phenyl, naphthyl, indolyl, benzothienyl, benzofuryl or benzoxazolyl group which may have 1 to 3 substituents selected from the group consisting of hydroxyl and lower alkyloxy groups, or a hydrogen atom; $R^2$ is a lower alkyl group, a benzyl group, a 4-hydroxybenzyl group, a 3-indolylmethyl group or a β-phenethyl group; and A is an optional residue of an amino acid selected from the group consisting of tryptophane, tyrosine, phenylalanine, homophenylalanine, naphthylalanine or $N^\omega$-nitroarginine, and their pharmaceutically acceptable salts. The compounds according to the present invention and their pharmaceutically acceptable salts exhibit an inhibitory activity against endothelin-converting enzyme, and are expected to be useful as a drug treating various diseases with which endothelin is concerned.

6 Claims, 1 Drawing Sheet

FIG.1

AMINOPHOSPONIC ACID DERIVATIVE

FIELD OF THE INVENTION

The present invention relates to novel compounds which exhibit an inhibitory activity against endothelin-converting enzyme, and uses of the novel compounds.

The compounds of the present invention and pharmaceutically acceptable salts thereof exhibit vasodilator and bronchodilator effects, and thus may be used in the field of medicine as a drug for the treatment of a disorder related to endothelin such as hypertension, pulmonary hypertension, Raynaud's disease, Buerger's disease, Takayasu's disease, Kawasaki's disease, diabetes, bronchial asthma, arteriosclerosis, acute renal failure, myocardial infarction, angina pectoris, cerebral vasospasm, cerebral infarction, endotoxin shock, endotoxin-induced multiple organ failure or disseminated intravascular coagulation, cyclosporin- or cisplatin-induced renal failure or hypertension, congestive heart failure, vascular restenosis, and inflammatory bowel diseases.

BACKGROUND OF THE INVENTION

It is known that endothelin is a polypeptide composed of 21 amino acid residues, is produced by endothelial cells of human or other mammals, and exhibits a potent vasoconstrictor effect and a prolonged, potent pressor action. It is also known that the production mechanism for endothelin begins with the biosynthesis of preproendothelin, which undergoes processing in the cells to become big endothelin, followed by the hydrolysis of the peptide bond between Trp21-Val22 of big endothelin by endothelin-converting enzyme to produce endothelin. It is further known that endothelin-converting enzyme itself is a phosphoramidon-sensitive neutral metalloprotease (Nature, Vol. 332, p.411–415, 1988; Biochem. Biophys. Res. Commun., Vol. 168, p.1128–1136, 1990; Ibid, Vol. 171, p.1192–1198, 1990; FEBS Letters, Vol. 272, p.166–170, 1990).

As reported, the levels of endothelin are clearly elevated in the blood of patients with essential hypertension, acute myocardial infarction, pulmonary hypertension, Raynaud's disease, atherosclerosis, subarachnoid hemorrhage, disseminated intravascular coagulation, Buerger's disease, Takayasu's disease, Kawasaki's disease, diabetes, or renal failure caused by administration of cisplatin, and also in the washing fluids of respiratory tract or the blood of asthma patients as compared with normal levels (Japan J. Hypertension, Vol. 12, p.79, 1989; J. of Vascular Medicine Biology, Vol. 2, p.207, 1990; J. of Am. Med. Association, Vol. 264, p.2868, 1990; The Lancet, Vol. 2, p.747–748, 1989, Vol. 2, p.1144–1147, 1990; J. of Int. Secr. Association, Vol. 67, p.421, 469–470, 1991).

Further, an increased sensitivity of the cerebral blood vessel to endothelin in an experimental model of cerebral vasospasm (Japan. Soc. Cereb. Blood Flow & Metabol., 1, 73 (1989)) and an improved renal function by the endothelin antibody in an acute renal failure model (J. Clin. Invest., 83, 1762–1767 (1989)), have been reported. Therefore, endothelin is assumed to be one of mediators causing acute renal failure or cerebral vasospasm following subarachnoid hemorrhage.

Further, it has become clear that endothelin is secreted not only by vascular endothelial cells, but also by tracheal epitherial cells or renal parenchymal cells (FEBS Letters, Vol. 255, p.129–132, 1989; FEBS Letters, Vol. 249, p.42–46, 1989).

It has also been discovered that endothelin regulates the release of endogenous physiologically active substances such as renin, atrial natriuretic peptide, endothelium-derived relaxing factor (EDRF), thromboxane $A_2$, prostacyclin, noradrenaline, angiotensin II, and substance P (Biochem. Biophys. Res. Commun., Vol. 157, p.1164–1168, 1988; Biochem. Biophys. Res. Commun., Vol. 155, p.167–172, 1989, Proc. Natl. Acad. Sci. USA, Vol. 85, p.9797–9800, 1989; J. of Cardiovasc. Pharmacol., Vol. 13, p.S89–S92, 1989; Japan J. Hypertension, Vol. 12, p.76, 1989; Neuroscience Letters, Vol. 102, p.179–184, 1989). In addition, endothelin also causes contraction of the smooth muscle of gastrointestinal tract and the uterine smooth muscle (FEBS Letters, Vol. 247, p.337–340, 1989; Eur. J. Pharmacol., Vol. 154, p.227–228, 1988; Biochem. Biophys. Res. Commun., Vol. 159, p.317–323, 1989).

Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)).

In addition, it was reported that cyclosporin remarkably increased endothelin secretion in the renal cell culture (LLC-PK1 cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Therefore, substances which inhibit endothelin-converting enzyme suppress overproduction of endothelin and thus may be considered to be effective in the prevention and treatment of the various diseases mentioned above. Nevertheless, aside from phosphoramidon, there have been no reports to date of any potent inhibitors of endothelin-converting enzyme.

Endothelin is an endogenous physiologically active substance which directly or indirectly (by regulating the liberation of various endogenous substances) causes sustained contraction of vascular or non-vascular smooth muscles. Its overproduction or over-secretion is believed to be one of pathogeneses for hypertension, pulmonary hypertension, Reynaud's disease, Buerger's disease, Takayasu's disease, Kawasaki's disease, diabetes, bronchial asthma, arteriosclerosis, acute renal failure, myocardial infarction, angina pectoris, cerebral vasospasm and cerebral infarction. In addition, it is suggested that endothelin serves as an important mediator involved in diseases such as endotoxin shock, endotoxin-induced multiple organ failure or disseminated intravascular coagulation, cyclosporin- or cisplatin-induced renal failure or hypertension, congestive heart failure, vascular restenosis, and inflammatory bowel diseases. Thus, an invention of an inhibitor of endothelin-converting enzyme would provide a novel method for the treatment of the various kinds of diseases mentioned above.

SUMMARY OF THE INVENTION

In order to achieve the objects described above, the inventors of the present invention synthesized and screened various aminophosphonic acid derivatives in search of compounds which exhibit inhibition activities against endothelin-converting enzyme. As a result, it has been found that the novel aminophosphonic acid derivatives of formula [I] shown below exhibit potent inhibition activities against endothelin-converting enzyme. Thus, the present invention has been completed on the basis of the above finding.

The present invention is, therefore, directed to a novel aminophosphonic acid derivative of formula [I]:

wherein n is an integer 2 or 3; $R^1$ represents a phenyl, naphthyl, indolyl, benzothienyl, benzofuryl or benzoxazolyl group which may have 1 to 3 substituents selected from the group consisting of hydroxyl and lower alkyloxy groups, or a hydrogen atom; $R^2$ represents a lower alkyl group, a benzyl group, a 4-hydroxybenzyl group, a 3-indolylmethyl group or a β-phenethyl group; and A represents an amino acid selected from the group consisting of tryptophan, tyrosine, phenylalanine, homophenylalanine, α-naphthylalanine and Nω-nitroarginine, or a pharmaceutically acceptable salt thereof.

In further aspects, the present invention relates to a useful method for the treatment of various types of disorders related to endothelin, such as hypertension, pulmonary hypertension, Raynaud's disease, Buerger's disease, Takayasu's disease, Kawasaki's disease, diabetes, bronchial asthma, arteriosclerosis, acute renal failure, myocardial infarction, angina pectoris, cerebral vasospasm, cerebral infarction, endotoxin shock, endotoxin-induced multiple organ failure or disseminated intravascular coagulation, cyclosporin- or cisplatin-induced renal failure or hypertension, congestive heart failure, vascular restenosis, and inflammatory bowel diseases.

DETAILED DESCRIPTION OF THE INVENTION

Unless otherwise defined, the term "lower alkyl group" used herein includes a linear or branched alkyl group consisting of 1–6 carbon atoms, for example, such as methyl, ethyl, propyl, isopropyl, butyl, isobutyl, tert-butyl, pentyl, isopentyl, hexyl, etc.

Compounds [I] of the present invention may form a pharmaceutically acceptable salt with an acid or base. The acid can be, for example, an inorganic acid such as hydrochloric acid, sulfuric acid, nitric acid or phosphoric acid, or an organic acid such as maleic acid or fumaric acid, and the base can be, for example, an inorganic base such as sodium hydroxide, potassium hydroxide, calcium hydroxide or barium hydroxide, or an organic base such as triethylamine. These salts may be produced according to conventional methods.

If compounds of formula [I] or their salts can form solvates or hydrates, these are also included in the present invention.

Compounds of formula [I] possess, at least, three asymmetric centers, allowing them to exist in a variety of stereoisomers. The present invention includes all such forms, as well as their mixtures such as racemates and diastereomeric mixtures thereof.

Preferred isomers have structures represented by formula [I] wherein A an L-amino acid selected from the group consisting of L-tryptophan, L-tyrosine, α-naphthyl-L-alanine and Nω-nitro-L-arginine.

The following is a description of a method for the production of novel aminophosphonic acid derivatives of the present invention.

A compound of the present invention [I] may be produced by subjecting to the cleavage of groups $R^3$ and $R^5$, and if necessary, conversion of $R^4$ to $R^1$, a compound of formula [II]:

wherein $R^3$ and $R^5$ each represents a lower alkyl group or a benzyl group which may have a substituent such as a nitro group or a methoxy group; $R^4$ represents a phenyl, naphthyl, protected or unprotected indolyl (typical examples of the protecting group include a formyl group, a t-butoxycarbonyl group, a benzyloxycarbonyl group, or a substituted or unsubstituted benzenesulfonyl group), benzothienyl, benzofuryl or benzoxazolyl group which may have 1 to 3 substituents selected from the group consisting of substituted or unsubstituted benzyloxy, t-butoxy, methoxymethoxy, trialkylsilyl, tetrahydropyran-2-yloxy, lower acyloxy and lower alkyloxy groups; and n, $R^2$ and A are as defined above.

The cleavage of $R^3$ may be effected by using a trimethylsilyl halide, preferably bromotrimethylsilane, in an inert solvent such as, for example, dichloromethane, or using a hydrogen halide, preferably hydrogen bromide, in an inert solvent such as, for example, acetic acid. The cleavage of $R^5$ may be effected by hydrolysis under acidic or basic conditions. If $R^3$ and $R^5$ are optionally substituted benzyl groups, their cleavage may be effected by either hydrolysis or a conventional debenzylation method. If $R^1$ is a hydroxy-substituted phenyl, naphthyl or 3-indolyl group, or an unsubstituted 3-indolyl group, such phenolic hydroxyl groups and/or the 1-NH on the indole ring may, if necessary, be protected with an appropriate protecting group. $R^4$ which can be converted to $R^1$ signifies a protected $R^1$ group wherein such phenolic hydroxyl groups and/or the 1-NH on the indole ring are protected with an appropriate protecting group. Therefore, conversion of $R^4$ to $R^1$ means to remove protecting groups for such phenolic hydroxyl groups and/or the 1-NH on the indole ring. The protecting group for a phenolic hydroxyl group may be an ether-forming protecting group such as, for example, optionally substituted benzyl, tert-butyl, methoxymethyl or tri-lower-alkylsilyl, an acetal-forming protecting group such as, for example, tetrahydropyranyl, or an ester-forming protecting group such as, for example, acetyl. The protecting group for the 1-NH on the indole ring may be, for example, formyl, tert-butoxycarbonyl, benzyloxycarbonyl or 4-methoxy-2,3,6-trimethylbenzene sulfonyl, etc. These protecting groups may be removed using a conventional method for each group. The cleavage of $R^3$ and $R^5$ and the conversion of $R^4$ to $R^1$ may be effected by an appropriately selected single reaction or series of reactions.

A compound of formula [II] may be produced by reacting a compound of formula [III]:

[III]

wherein $R^2$, $R^5$ and A are as defined above, or a salt thereof, with an aldehyde represented by the general formula: $R^4$—$(CH_2)_n$—CHO, wherein $R^4$ and n are as defined above, and then treating the product of this reaction with a phosphite represented by the general formula: $(R^3O)_2P(O)H$, wherein $R^3$ is as defined above.

A compound of formula [II] may also be produced by condensing an amino acid ester derivative of formula [V]

[V]

wherein $R^5$ and A are as defined above, with a compound of formula [IV]:

[IV]

wherein $R^4$, $R^2$, $R^3$ and n are as defined above. The reaction is preferably conducted in an inert solvent such as, for example, dichloromethane, in the presence of a condensing auxiliary agent such as 1-hydroxybenzotriazole, using a condensing agent such as, for example, dicyclohexylcarbodiimide or 1-ethyl-3-(3-dimethylaminopropyl)carbodiimide hydrochloride.

The compound of formula [IV] may be produced by reacting a compound of formula [VI]:

[VI]

wherein $R^6$ is a lower alkyl group or an optionally substituted benzyl group and $R^2$ is as defined above, or a salt thereof, with an aldehyde of the general formula: $R^4$—$(CH_2)_n$—CHO, wherein $R^4$ and n are as described above, treating the product of this reaction with a phosphite of the general formula: $(R^3O)_2P(O)H$, wherein $R^3$ is as defined above, and finally causing cleavage of the carboxy-protecting group $R^6$. The cleavage of $R^6$ may be effected by hydrolysis under acidic or alkaline conditions. If $R^6$ is an optionally substituted benzyl group, hydrolysis or a conventional debenzylation method may be used.

Further, a compound of formula [IV] may be produced by reacting a compound of formula [VII]:

[VII]

wherein $R^4$, $R^3$ and n are as defined above, with a compound of formula [VIII]:

[VIII]

wherein X is a leaving group, preferably a trifluoromethylsulfonyloxy group; and $R^2$ and $R^6$ are as defined above, and then causing cleavage of the carboxy-protecting group $R^6$.

The compounds of the present invention may be used in the form of drug formulations suitable for parenteral, oral or external administration by being mixed with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin-converting enzyme inhibitor varies depending upon the manner of administration, the age and body weight of the patient and the condition of the patient to be treated. However, a typical administration method for an adult is oral administration or parenteral administration. The daily dose in the case of oral administration to an adult patient is from 0.5 to 100 mg/kg body weight, preferably 1 to 50 mg/kg, and the daily dose in the case of parenteral administration is from 0.1 to 50 mg/kg, preferably 0.1 to 25 mg/kg.

The following Examples, Referential Examples and Test Examples illustrate the present invention more specifically. It should be understood that the present invention is not limited to these examples alone.

EXAMPLE 1

Production of a tripotassium salt of N-[N-(3-phenyl-1-phosphonopropyl)-L-leucyl]-L-tryptophan (i) N-[N-(1-dibenzyloxyphosphoryl-3-phenylpropyl)-L-leucyl]-L-tryptophan benzyl ester A mixture of L-leucyl-L-tryptophan benzyl ester (1.17 g) and 3-phenylpropionaldehyde (0.40 g) in benzene (10 ml) was heated to reflux in a Dean-Stark apparatus for 2 hours. After cooling, dibenzyl phosphite (0.87 g) and acetonitrile (7 ml) were added to the mixture and the resulting solution was stirred at 80° C. for 19 hours. After being cooled to room temperature, the mixture was concentrated under reduced pressure, the residue was separated and purified by silica gel chromatography (hexane:ethyl acetate=2:1; chloroform:ethyl acetate=5:1), and two diastereomers of the title compound were obtained as colorless oil (a: 114 mg, b: 272 mg).

(ii) A tripotassium salt of N-[N-(3-phenyl-1-phosphonopropyl)-L-leucyl]-L-tryptophan Isomer A Isomer a of N-[N-(1-benzyloxyphosphoryl-3-phenylpropyl)-L-leucyl]-L-tryptophan benzyl ester (105 mg) was dissolved in 95% ethanol (10 ml), to which 10% palladium-carbon (50 mg) was added, and the mixture was vigorously stirred under an atmospheric pressure of hydrogen at room temperature for 3.5 hours. The palladium-carbon was then filtered off, and 1N potassium hydroxide (0.40 ml) was added to the filtrate. The solvent was distilled off under reduced pressure, and the residue was triturated with ethyl ether (20 ml) to give the title compound as a light yellow powder (72 mg).

Melting point: 235° C. (decomposition)

IR (KBr, cm$^{-1}$): 3376, 2962, 1599, 1530, 1458, 1410, 1056, 975, 744

High resolution FAB-MS (m/e, as ($C_{26}H_{31}K_3N_3O_6P$+H)+): Calculated: 630.0940 Found: 630.0957

$^1$H-NMR (300 MHz, $D_2O$, δ ppm): 0.78(3H,d,J=6.6 Hz), 0.81(3H,d,J=6.6 Hz), 1.20–1.90(5H,m), 2.25–2.60(3H,m), 3.16(1H,dd,J=9.2 Hz,15.6 Hz), 3.27–3.37(2H,m), 4.66(1H,dd,J=4.7 Hz,9.2 Hz), 6.99–7.28(8H,m), 7.42(1H,d,J=7.6 Hz), 7.71(1H,d,J=7.6 Hz)

$^{31}$P-NMR (121 MHz, $D_2O$, δ ppm): 19.02

Isomer B

Isomer b of N-[N-(1-benzyloxyphosphoryl-3-phenylpropyl)-L-leucyl]-L-tryptophan benzyl ester (261 mg) was treated in the same manner as described with Isomer a to give the title compound as a light yellow powder (190 mg).

Melting point: 230° C. (decomposition):

IR (KBr, cm$^{-1}$) 3418, 2956, 1644, 1596, 1527, 1458, 1401, 1059, 972, 741

High resolution FAB-MS (m/e, as ($C_{26}H_{31}K_3N_3O_6P$+H)+): Calculated: 630.0940 Found: 630.0931

$^1$H-NMR (300 MHz, $D_2O$, δ ppm): 0.77(3H,d,J=6.3 Hz), 0.82(3H,d,J=6.3 Hz), 1.20–1.57(4H,m), 1.83–2.00(1H,m), 2.07–2.19(1H,m), 2.43–2.55(1H,m), 2.25–2.35(1H,m), 3.09(1H,dd,J=8.9 Hz,14.8 Hz), 3.30–3.40(2H,m), 4.53(1H,dd,J=4.6 Hz,8.9 Hz), 7.09–7.30(8H,m), 7.43(1H,d,J=7.3 Hz), 7.72(1H,d,J=7.3 Hz)

$^{31}$P-NMR (121 MHz, $D_2O$, δ ppm):20.23

EXAMPLE 2

Production of a tripotassium salt of N-{N-[3-(1-naphthyl)-1-phosphonopropyl]-L-leucyl}-L-tryptophan (i) N-{N-[1-benzyloxyphosphoryl-3-(1-naphthyl)propyl]-L-leucyl}-L-tryptophan benzyl ester A mixture of L-leucyl-L-tryptophan benzyl ester (408 mg) and 3-(1-naphthyl)propionaldehyde (220 mg) in toluene (10 ml) was heated to reflux in a Dean-Stark apparatus for 2 hours. After cooling, dibenzyl phosphite (252 mg) and acetonitrile (10 ml) were added to the mixture and the resulting solution was stirred at 100° C. for 16 hours. After being cooled to room temperature, the mixture was concentrated under reduced pressure. The residue was separated and purified by silica gel chromatography (chloroform:ethyl acetate=5:1) to give two diastereomers of the title compound as colorless oil (a: 58 mg, b: 95 mg).

(ii) A tripotassium salt of N-{N-[3-(1-naphthyl)-1-phosphonopropyl]-L-leucyl}-L-tryptophan Isomer A Isomer a of N-{N-[1-dibenzyloxyphosphoryl-3-(1-naphthyl)propyl]-L-leucyl}-L-tryptophan benzyl ester (54 mg) was dissolved in 95% ethanol (10 ml), to which 10% palladium-carbon (50 mg) was added, and the mixture was stirred overnight under an atmospheric pressure of hydrogen at room temperature. The palladium-carbon was then filtered off, and 1N potassium hydroxide (193 μl) was added to the filtrate. The solvent was distilled off under reduced pressure to give the title compound as a light yellow powder (36 mg).

IR (KBr, cm$^{-1}$): 3364, 2956, 1635, 1602, 1422, 1308, 1059, 972, 741

High resolution FAB-MS (m/e, as ($C_{30}H_{33}K_3N_3O_6P$+H)+): Calculated: 680.1096 Found: 680.1118

$^1$H-NMR (300 MHz, $D_2O$, δ ppm): 0.71(3H,d,J=5.9 Hz), 0.73(3H,d,J=5.9 Hz), 1.21–1.50(3H,m), 1.62–2.06(2H,m), 2.49–2.61(1H,m), 2.77–2.95(2H,m), 3.00–3.35(3H,m), 4.58–4.68(1H,m), 6.99–8.01(12H,m)

$^{31}$P-NMR (121 MHz, $D_2O$, δ ppm): 19.19

Isomer B

Isomer b of N-{N-[1-benzyloxyphosphoryl-3-(1-naphthyl)propyl]-L-leucyl}-L-tryptophan benzyl ester (91 mg) was treated in the same manner as described with Isomer a to give the title compound as a light yellow powder (64 mg).

IR (KBr, cm$^{-1}$): 3424, 2956, 1635, 1599, 1401, 1059, 972, 741

High resolution FAB-MS (m/e, as ($C_{30}H_{33}K_3N_3O_6P$+H)+): Calculated: 680.1096 Found: 680.1112

$^1$H-NMR (300 MHz, $D_2O$, δ ppm): 0.78(3H,d,J=5.7 Hz), 0.80(3H,d,J=5.7 Hz), 1.22-1.53(3H,m), 1.55-1.84(1H,m), 1,96-2.15(1H,m), 2.40-2.53(1H,m), 2.58-

2.74(1H,m), 2.87-3.13(2H,m), 3.23-3.40(2H,m), 4.51(1H,dd,J=4.9 Hz,8.4 Hz), 6.93-8.00(12H,m)

$^{31}$P-NMR (121 MHz, D$_2$O, δ ppm): 20.42

Each compound described in the following Examples 3-11 was prepared according to the same procedures as described Example 2 using each corresponding dipeptide benzyl ester, and an aldehyde whose functional groups had been protected if necessary, as starting materials.

EXAMPLE 3

A tripotassium salt of N-[N-[3-(4-methoxyphenyl)-1-phosphonopropyl]-L-leucyl]-L-tryptophan

Isomer A

IR (KBr, cm$^{-1}$): 3412, 2956, 1638, 1596, 1518, 1404, 1059, 975

High resolution FAB-MS (m/e, as (C$_{27}$H$_{33}$K$_3$N$_3$O$_7$P+H)$^+$): Calculated: 660.1046 Found: 660.1025

$^1$H-NMR (300 MHz, D$_2$O, δ ppm): 0.78(3H,d,J=6.8 Hz), 0.80(3H,d,J=6.8 Hz), 1.20-1.90(5H,m), 2.18-2.56(3H,m), 3.15(1H,dd,J=9.3 Hz,15.0 Hz), 3.25-3.38(2H,m), 3.76(3H,s), 4.66(1H,dd,J=4.3 Hz,9.3 Hz), 6.80(2H,d,J=7.1 Hz), 6.92(2H,d,J=7.1 Hz), 7.10-7.24(2H,m), 7.25(1H,s), 7.41(1H,d,J=7.8 Hz), 7.70(1H,d,J=7.8 Hz)

$^{31}$P-NMR (121 MHz, D$_2$O, δ ppm): 19.05

Isomer B

IR (KBr, cm$^{-1}$): 3430, 2956, 1647, 1596, 1515, 1407, 1059, 972

High resolution FAB-MS (m/e, as (C$_{27}$H$_{33}$K$_3$N$_3$O$_7$P+H)$^+$): Calculated: 660.1046 Found: 660.1028

$^1$H-NMR (300 MHz, D$_2$O, δ ppm): 0.76(3H,d,J=6.6 Hz), 0.80(3H,d,J=6.6 Hz), 1.15-1.52(3H,m), 1.70-2.00(2H,m), 2.00-2.20(1H,m), 2.22-2.37(1H,m), 2.37-2.52(1H,m), 3.08(1H,dd,J=8.8 Hz,14.6 Hz), 3.26-3.40(2H,m), 3.65(3H,s), 4.51(1H,dd,J=4.7 Hz,8.8 Hz), 6.86(2H,d,J=8.6 Hz), 7.03(2H,d,J=8.6 Hz), 7.07-7.22(2H,m), 7.26(1H,s), 7.42(1H,d,J=7.9 Hz), 7.70(1H,d,J=7.9 Hz)

$^{31}$P-NMR (121 MHz, D$_2$O, δ ppm): 20.20

EXAMPLE 4

A tripotassium salt of N-[N-[3-(4-hydroxyphenyl)-1-phosphonopropyl]-L-leucyl]-L-tryptophan

Isomer A

IR (KBr, cm$^{-1}$): 3418, 2962, 1596, 1518, 1404, 1056, 972

High resolution FAB-MS (m/e, as (C$_{26}$H$_{31}$K$_3$N$_3$O$_7$P+H)$^+$): Calculated: 646.0889 Found: 646.0813

$^1$H-NMR (300 MHz, D$_2$O, δ ppm): 0.79(3H,d,J=6.5 Hz), 0.81(3H,d,J=6.5 Hz), 1.20-1.85(5H,m), 2.10-2.47(3H,m), 3.17(1H,dd,J=9.3 Hz,15.2 Hz), 3.32(1H,dd,J=5.1 Hz,15.2 Hz), 3.25-3.40(1H,m), 4.66(1H,dd,J=5.1 Hz,9.3 Hz), 6.56(2H,d,J=8.2 Hz), 6.81(2H,d,J=8.2 Hz), 7.10-7.30(3H,m), 7.44(1H,d,J=7.4 Hz), 7.72(1H,d,J=7.4 Hz)

$^{31}$P-NMR (121 MHz, D$_2$O, δ ppm): 19.10

Isomer B

IR (KBr, cm$^{-1}$): 3424, 2956, 1647, 1596, 1518, 1053, 969

High resolution FAB-MS (m/e, as (C$_{26}$H$_{31}$K$_3$N$_3$O$_7$P+H)$^+$): Calculated: 646.0889 Found: 646.0822

$^1$H-NMR (300 MHz, D$_2$O, δ ppm): 0.77(3H,d,J=6.6 Hz), 0.81(3H,d,J=6.6 Hz), 1.15-1.55(3H,m), 1.68-2.10(3H,m), 2.20-2.45(2H,m), 3.09(1H,dd,J=8.7 Hz,14.9 Hz), 3.34(1H,dd,J=4.6 Hz,14.9 Hz), 3.30-3.43(1H,m), 4.53(1H,dd,j=4.6 Hz,8.7 Hz), 6.70(2H,d,J=8.4 Hz), 6.94(2H,d,J=8.4 Hz), 7.08-7.25(2H,m), 7.27(1H,s), 7.43(1H,d,J=7.7 Hz), 7.72(1H,d,J=7.7 Hz)

$^{31}$P-NMR (121 MHz, D$_2$O, δ ppm): 19.88

EXAMPLE 5

A tripotassium salt of N-[N-(4-phenyl-1-phosphonobutyl)-L-leucyl]-L-tryptophan

Isomer A

IR (KBr, cm$^{-1}$): 3412, 2956, 1638, 15.99, 1404, 1053, 975, 741

High resolution FAB-MS (m/e, as (C$_{27}$H$_{33}$K$_3$N$_3$O$_7$P+H)$^+$): Calculated: 644.1096 Found: 644.1024

$^1$H-NMR (300 MHz, D$_2$O, δ ppm): 0.73(3H,d,J=6.7 Hz), 0.75(3H,d,J=6.7 Hz), 1.06-1.82(7H,m), 2.28-2.51(3H,m), 3.07-3.22(2H,m), 3.30(1H,dd,J=4.9 Hz,15.1 Hz), 4.61(1H,dd,J=4.9 Hz,8.9 Hz), 6.97-7.77(10H,m), $^{31}$P-NMR (121 MHz, D$_2$O, δ ppm): 19.32

Isomer B

IR (KBr, cm$^{-1}$): 3358, 2956, 1641, 1596, 1530, 1455, 1059, 972, 741

High resolution FAB-MS (m/e, as (C$_{27}$H$_{33}$K$_3$N$_3$O$_7$P+H)$^+$): Calculated: 644.1096 Found: 644.1117

$^1$H-NMR (300 MHz, D$_2$O, δ ppm): 0.76(3H,d,J=6.8 Hz), 0.78(3H,d,J=6.8 Hz), 1.08-1.78(7H,m), 2.21-2.52(3H,m), 3.05(1H,dd,J=8.6 Hz,14.3 Hz), 3.21-3.42(2H,m), 4.45(1H,dd,J=4.7 Hz,8.6 Hz), 7.07-7.77(10H,m), $^{31}$P-NMR (121 MHz, D$_2$O, δ ppm): 20.79

EXAMPLE 6

A tripotassium salt of N-[N-[3-(3-indolyl)-1-phosphonopropyl]-L-leucyl]-L-tryptophan (a mixture of diastereomers)

IR (KBr, cm$^{-1}$): 3424, 2956, 1644, 1596, 1533, 1458, 1401, 1059, 972, 741

High resolution FAB-MS (m/e, as (C$_{28}$H$_{32}$K$_3$N$_3$O$_6$P+H)$^+$): Calculated: 669.1049 Found: 669.1077

$^1$H-NMR (300 MHz, D$_2$O, δ ppm): 0.70-0.98(6H,m), 1.14-1.47(2H,m), 1.55-2.14(3H,m), 2.35-2.80(3H,m), 3.02-3.37(3H,m), 4.50+4.61(1H,dd×2,J=5.1 Hz, 8.6 Hz), 6.86-7.74(10H,m)

$^{31}$P-NMR (121 MHz, D$_2$O, δ ppm): 20.53

EXAMPLE 7

A tripotassium salt of
N-[N-(1-phosphonobutyl)-L-leucyl]-L-tryptophan (a mixture of diastereomers)

IR (KBr, cm$^{-1}$): 3436, 2962, 1650, 1596, 1530, 1461, 1398, 1161, 1059, 741

High resolution FAB-MS (m/e, as (C$_{21}$H$_{29}$K$_3$N$_3$O$_6$P+H)$^+$): Calculated: 568.0783 Found: 568.0793

$^1$H-NMR (300 MHz, D$_2$O, δ ppm): 0.50+0.61(3H,t×2,J=7.0 Hz,J=7.0 Hz), 0.69–0.89(6H,m), 0.91–1.35(3H,m), 1.38–1.63(4H,m), 1.96–2.08+2.43–2.57(1H,m×2), 2.93+3.08(1H,t+dd,J=12.4 Hz,J=8.0 Hz,12.4 Hz), 3.23–3.42(2H,m), 3.80+4.24(1H,t+2, J=6.6 Hz,J=6.6 Hz), 7.01–7.24(3H,m), 7.40(1H,d,J=7.8 Hz), 7.64+7.69(1H,d×2, J=7.8 Hz,J=7.8 Hz)

$^{31}$P-NMR (121 MHz, D$_2$O, δ ppm): 12.25, 13.06

EXAMPLE 8

A tripotassium salt of
N-[N-(3-phenyl-1-phosphonopropyl)-L-isoleucyl]-L-tryptophan

Isomer A

IR (KBr, cm$^{-1}$): 3382, 2968, 1599, 1524, 1458, 1404, 1056, 975, 744

High resolution FAB-MS (m/e, as (C$_{26}$H$_{31}$K$_3$N$_3$O$_6$P+H)$^+$): Calculated: 630.0940 Found: 630.0959

$^1$H-NMR (300 MHz, D$_2$O, δ ppm): 0.70–0.85(6H,m), 1.00–1.40(2H,m), 1.48–1.95(3H,m), 2.30–2.62(3H,m), 3.10–3.24(2H,m), 3.32(1H,dd,J=5.0 Hz,15.0 Hz), 4.63(1H,dd,J=4.7 Hz,9.4 Hz), 7.03–7.39(8H,m), 7.42(1H,d,J=7.5 Hz), 7.71(1H,d,J=7.5 Hz)

$^{31}$P-NMR (121 MHz, D$_2$O, δ ppm): 19.12

Isomer B

IR (KBr, cm$^{-1}$): 3424, 2968, 1647, 1599, 1530, 1458, 1398, 1059, 972, 741

High resolution FAB-MS (m/e, as (C$_{26}$H$_{31}$K$_3$N$_3$O$_6$P+H)$^+$): Calculated: 630.0940 Found: 630.0942

$^1$H-NMR (300 MHz, D$_2$O, δ ppm): 0.67–0.81(6H,m), 0.88–1.22(2H,m), 1.46–1.65(2H,m), 1.85–2.04(1H,m), 2.25–2.41(2H,m), 2.46–2.60(1H,m), 3.05–3.18(2H,m), 3.33(1H,dd,J=4.7 Hz,14.9 Hz), 4.57(1H,dd,J=4.7 Hz,9.0 Hz), 7.06–7.47(8H,m), 7.43(1H,d,J=7.0 Hz), 7.73(1H,d,J=7.0 Hz)

$^{31}$P-NMR (121 MHz, D$_2$O, δ ppm): 19.74

EXAMPLE 9

A tripotassium salt of
N-[N-(3-phenyl-1-phosphonopropyl)-L-norleucyl]-L-tryptophan

Isomer A

IR (KBr, cm$^{-1}$): 3424, 2932, 1644, 1599, 1407, 1062, 972, 741

High resolution FAB-MS (m/e, as (C$_{26}$H$_{31}$K$_3$N$_3$O$_6$P+H)$^+$): Calculated: 630.0940 Found: 630.0964

$^1$H-NMR (300 MHz, D$_2$O, δ ppm): 0.77(3H,t,J=7.4 Hz), 0.70–2.00(8H,m), 2.30–2.57(3H,m), 3.15(1H,dd,J=9.9 Hz,15.2 Hz), 3.25–3.40(2H,m), 4.64(1H,dd,J=4.5 Hz,9.9 Hz), 7.00–7.50(9H,m), 7.72(1H,dd,J=1.2 Hz,7.0 Hz)

$^{31}$P-NMR (121 MHz, D$_2$O, δ ppm): 19.42

Isomer B

IR (KBr, cm$^{-1}$): 3430, 2956, 1644, 15.99, 1401, 1059, 972, 741

High resolution FAB-MS (m/e, as (C$_{26}$H$_{31}$K$_3$N$_3$O$_6$P+H)$^+$): Calculated: 630.0940 Found: 630.0989

$^1$H-NMR (300 MHz, D$_2$O, δ ppm): 0.78(3H,t,J=7.3 Hz), 0.85–2.02(8H,m), 2.10–2.25(1H,m), 2.25–2.35(1H,m), 2.40–2.60(1H,m), 3.11(1H,dd,J=8.8 Hz,14.6 Hz), 3.25–3.40(2H,m), 4.53(1H,dd,J=4.7 Hz,8.8 Hz), 7.05–7.50(9H,m), 7.72(1H,dd,J=1.2 Hz,7.0 Hz)

$^{31}$P-NMR (121 MHz, D$_2$O, δ ppm): 20.55

EXAMPLE 10

A tripotassium salt of
N-[N-(3-phenyl-1-phosphonopropyl)-L-phenylalanil]-L-tryptophan

Isomer A

IR (KBr, cm$^{-1}$): 3376, 1635, 1602, 1455, 1059, 972, 744, 702

High resolution FAB-MS (m/e, as (C$_{29}$H$_{29}$K$_3$N$_3$O$_6$P+H)$^+$): Calculated: 664.0783 Found: 664.0765

$^1$H-NMR (300 MHz, D$_2$O, δ ppm): 1.40–2.00(2H,m), 2.35(2H,t,J=8.5 Hz), 2.45–2.60(1H,m), 2.74(2H,d,J=6.7 Hz), 3.13(1H,dd,J=9.0 Hz,15.0 Hz), 3.27(1H,dd,J=4.7 Hz,15.0 Hz), 3.55–3.65(1H,m), 4.44–4.54(1H,m), 7.00–7.32(13H,m), 7.42(1H,d,J=8.1 Hz), 7.65(1H,d,J=7.6 Hz)

$^{31}$P-NMR (121 MHz, D$_2$O, δ ppm): 19.45

Isomer B

IR (KBr, cm$^{-1}$): 3424, 1650, 1599, 1563, 1059, 972, 744, 702

High resolution FAB-MS (m/e, as (C$_{29}$H$_{29}$K$_3$N$_3$O$_6$P+H)$^+$): Calculated: 664.0783 Found: 664.0781

$^1$H-NMR (300 MHz, D$_2$O, δ ppm): 1.35–1.57(1H,m), 1.78–2.00(1H,m), 2.10–2.50(3H,m), 2.79(1H,dd,J=7.0 Hz,13.4 Hz), 2.98(1H,dd,J=5.1 Hz,13.4 Hz), 3.05(1H,dd,J=5.2 Hz,14.6 Hz), 3.13(1H,dd,J=7.2 Hz,14.6 Hz), 3.71(1H,dd,J=5.2 Hz,7.2 Hz), 4.43(1H,dd,J=5.1 Hz,7.0 Hz), 6.88(1H,s), 7.00–7.60(14H,m)

$^{31}$P-NMR (121 MHz, D$_2$O, δ ppm): 20.54

EXAMPLE 11

A tripotassium salt of
N-[N-(3-phenyl-1-phosphonopropyl)-L-leucyl]-L-tryptophan (a mixture of diastereomers)

IR (KBr, cm$^{-1}$): 3430, 2962, 1641, 1596, 1533, 1458, 1407, 1059, 972, 741, 705

High resolution FAB-MS (m/e, as (C$_{26}$H$_{31}$K$_3$N$_3$O$_6$P+H)$^+$): Calculated: 630.0940 Found: 630.0941

$^1$H-NMR (300 MHz, CD$_3$OD, δ ppm): 0.76–0.94(6H,m), 1.10–1.46(2H,m), 1.57–2.15(3H,m), 2.49–2.73(3H,m), 3.04–3.54(3H,m), 4.51+4.61(1H,dd×2, J=4.8 Hz,6.7 Hz,J=4.4 Hz,9.1 Hz), 6.89–7.34(9H,m), 7.60+7.63(1H,d×2,J=7.3 Hz,J=7.6 Hz)

$^{31}$P-NMR (121 MHz, D$_2$O, δ ppm): 17.93, 18.24

EXAMPLE 12

Production of a trisodium salt of
N-[N-(3-phenyl-1-phosphonopropyl)leucyl]-L-tyrosine (i) N-(1-dibenzyloxyphosphoryl-3-phenylpropyl)-L-leucine benzyl ester A mixture of 4.5 g of L-leucine benzyl ester and 2.7 g of 3-phenylpropionaldehyde in 30 ml of toluene was heated to reflux in a Dean-Stark apparatus for 2 hours. The mixture was allowed to cool, and 5.3 g of dibenzyl phosphite was added. Then the mixture was stirred at 80° C. for 15 hours. The mixture was refluxed for additional 6 hours after further addition of. After the mixture was allowed to cool, the solvent was distilled off under reduced pressure, and the residue was purified by silica gel chromatography to yield the title compound as a light-yellow oil (300 mg).

(ii) N-(1-dibenzyloxyphosphoryl-3-phenylpropyl)-leucine

N-(1-dibenzyloxyphosphoryl-3-phenylpropyl)-L-leucine benzyl ester (167 mg) was dissolved in 1.0 ml of ethanol, and the resulting solution was cooled to 0° C., and 0.55 ml of 1N potassium hydroxide was added to the solution. Then, the mixture was stirred at the same temperature for 40 minutes, and then at room temperature overnight. The reaction mixture was diluted with 10 ml of water, and the pH was adjusted to 4 by the addition of 0.6 ml of 1N hydrochloric acid, and the mixture was extracted with ethyl acetate (10 ml×3). The combined ethyl acetate extracts were washed with brine, and then dried over anhydrous magnesium sulfate. The solvent was distilled off under reduced pressure to yield the title compound as a mixture of four stereoisomers (140 mg).

(iii) N-[N-(1-dibenzyloxyphosphoryl-3-phenylpropyl)-leucyl]-L-tyrosine benzyl ester A solution of 140 mg of N-(1-dibenzyloxyphosphoryl-3-phenylpropyl)-leucine and 137 mg of L-tyrosine benzyl ester p-toluenesulfonate in 3 ml of dichloromethane was cooled to 0° C. Then 43 μl of triethylamine, 42 mg of 1-hydroxybenzotriazole monohydrate and 60 mg of 1-ethyl-3-(3-dimethylaminopropyl)-carbodiimide hydrochloride was added to the solution. The mixture was stirred at 0° C. for 30 minutes and then at room temperature for 3 hours. The reaction mixture was diluted with 50 ml of ethyl acetate, and the diluted solution was successively washed with a saturated aqueous solution of sodium bicarbonate, 1N hydrochloric acid and brine and then dried over anhydrous magnesium sulfate. Then the solvent was distilled off under reduced pressure, and the residue was purified by silica gel chromatography (hexane: ethyl acetate=1:2) to yield the title compound as a mixture of four stereoisomers (157 mg).

(iv) A tripotassium salt of
N-[N-(3-phenyl-1-phosphonopropyl)leucyl]-L-tyrosine

To a solution of 92 mg of N-[N-(1-dibenzyloxyphosphoryl-3-phenylpropyl)-leucyl]-L-tyrosine benzyl ester in 95% ethanol (2 ml) was added 48 mg of 10% Pd—C, after which the mixture was stirred vigorously under an atmospheric pressure of hydrogen at room temperature for 1 hour. The Pd—C was filtered off, and 362 μl of 1N potassium hydroxide was added to the filtrate. The solvent was distilled off to yield the title compound as a light-yellow powder which was a mixture of four stereoisomers (77 mg).

IR (KBr. cm$^{-1}$): 3352, 2956, 1650, 1599, 1521, 1398, 1056 and 972

High resolution FAB-MS (m/e, as $C_{24}H_{30}K_3N_2O_7P+H)^+$): Calculated: 607.0780 Found: 607.0756

$^1$H-NMR (300 MHz, CD$_3$OD, δ ppm): 0.80+0.82(3H,d×2,J=6.5 Hz), 0.90+0.92(3H,d×2, J=6.5 Hz), 1.30–2.20(4H,m), 2.40–3.02(4H,m), 3.02–3.50(3H,m), 4.25–4.50(1H,m), 6.58(2H,d,J=8,1 Hz), 6.88–7.30(7H,m)

$^{31}$P-NMR (121 MHz, CD$_3$OD, δ ppm): 20.66, 21.19

EXAMPLE 13

Production of
N-[N-(3-phenyl-1-phosphonoproryl)-leucyl]-3-(α-naphthyl)-L-alanine (i) N-(1-diethoxyphosphoryl-3-phenylpropyl)-leucine benzyl ester A mixture of 5.90 g of L-leucine benzyl ester p-toluenesulfonate, 2.01 g of 3-phenylpropionaldehyde and 2.09 ml of triethylamine in 100 ml of toluene was heated to reflux in a Dean-Stark apparatus for 2 hours. The mixture was allowed to cool, and then 1.93 ml of diethyl phosphite was added to the mixture. Then the mixture was heated to reflux for 27 hours, and then allowed to cool. The mixture was successively washed with 100 ml of water, 50 ml of 1N hydrochloric acid and 50 ml of a saturated aqueous solution of sodium bicarbonate. The organic layer was dried over anhydrous magnesium sulfate. The solvent was distilled off under reduced pressure, and the residue was purified by silica gel chromatography (chloroform: ethyl acetate=10: 1, and hexane: ethyl acetate=1: 1) to yield the title compound as a mixture of stereoisomers, a light-yellow oil (1.87 g).

(ii) N-(1-diethoxyphosphoryl-3-phenylpropyl)-leucine

To a solution of 445 mg of N-(1-diethoxyphosphoryl-3-phenylpropyl)-leucine benzyl ester in 10 ml of ethanol was added 100 mg of 10% Pd—C, after which the mixture was stirred vigorously under atmospheric pressure of hydrogen at room temperature for 24 hours. The Pd—C was filtered off, and the solvent was distilled off to yield the title compound as a light-yellow oil (356 mg).

(iii) N-[N-(1-diethoxyphosphoryl-3-phenylpropyl)leucyl]-3-(α-naphthyl)-L-alanine tert-butyl ester A solution of 61 mg of N-(1-diethoxyphosphoryl-3-phenylpropyl)-leucine and 39 mg of 3-(α-naphthyl)-L-alanine tert-butyl ester in 1.0 ml of dichloromethane was cooled to 0° C. Then 26 mg of 1-hydroxybenzotriazole monohydrate and 34 mg of 1-ethyl-3-(3-dimethylaminopropyl)-carbodiimide hydrochloride was added to the solution which was stirred at 0° C. for 1 hour and then at room temperature for 3 hours. The reaction mixture was diluted with 15 ml of dichloromethane, and the diluted solution was washed with 15 ml of a saturated aqueous solution of sodium bicarbonate and then dried over anhydrous magnesium sulfate. Then, the solvent was distilled off under reduced pressure, and the residue was separated and purified by silica gel chromatography (hexane: ethyl acetate=1:1) to yield the title compound as two mixtures each of which are composed of two stereoisomers (42 mg of a/b mixture, 35 mg of c/d/mixture). (iv) N-[N-(3-phenyl-phosphonopropyl)leucyl]-3-(α-naphthyl)-L-alanine Mixture of Isomers A and B A mixture of Isomers a and b of N-[N-(1-diethoxyphosphoryl-3-phenylpropyl)-leucyl]-3-(α-naphthyl)-L-alanine tert-butyl ester (37 mg) was dissolved in 0.50 ml of a 30% solution of hydrogen bromide in acetic acid, and the solution was stirred at room temperature for 21 hours. The reaction mixture was concentrated under reduced pressure, and the residue was triturated with 1 ml of water to yield the title compound as a colorless powder (28 mg). Analysis by high performance liquid chromatography [ODS column, mobile phase: water-/acetonitrile mixed solvent containing 0.1% trifluoroacetic acid (water/acetonitrile=¼→4/1) showed that the product is a 59:41 mixture of stereoisomers A and B.

IR (KBr, cm$^{-1}$): 3412, 3064, 2962, 1689, 1185, 1083 and 777

High resolution FAB-MS (m/e, as $C_{28}H_{35}N_2O_6P+H)^+$): Calculated: 527.2311
Found: 527.2307

$^1$H-NMR (300 MHz, D$_2$NaOD, δ ppm): 0.58+0.85(6H,m), 0.93+1.46(3H,m), 1.60-2.05(2H,m), 2.38-2.82(3H,m), 3.13-3.80(3H,m), 4.65-4.85(1H,m), 7.18-8.30(12H,m)

$^{31}$P-NMR (121 MHz, D$_2$O-NaOD, δ ppm): 19.28

Mixture of Isomers C and D

A mixture of Isomers c and d of N-[N-(1-diethoxyphosphoryl-3-phenylpropyl)-leucyl]-3-(α-naphthyl)-L-alanine tert-butyl ester (35 mg) was dissolved in 0.50 ml of a 30% solution of hydrogen bromide in acetic acid, and the solution was stirred at room temperature for 20 hours. The reaction mixture was concentrated under reduced pressure, and the residue was triturated with 1 ml of water to yield the title compound as a colorless powder (27 mg). Analysis by high performance liquid chromatography [ODS column, mobile phase: water-/acetonitrile mixed solvent containing 0.1% trifluoroacetic acid (water/acetonitrile=¼→4/1) showed that the product is a 57:43 mixture of stereoisomers C and D.

IR (KBr, cm$^{-1}$): 3424, 2962, 1686, 1557, 1458, 1170, 1083, 777 and 699

High resolution FAB-MS (m/e, as $C_{28}H_{35}N_2O_6P+H)^+$): Calculated: 527.2311 Found: 527.2301

$^1$H-NMR (300 MHz, D$_2$O-NaOD, δ ppm): 0.59+0.82(6H,m), 1.00+2.02(5H,m), 2.20-2.70(3H,m), 3.15-3.80(3H,m), 4.63-4.85(1H,m), 7.13-8.30(12H,m)

$^{31}$P-NMR (121 MHz, D$_2$O-NaOD, δ ppm): 20.33

EXAMPLE 14

Production of N$^\omega$-nitro-N$^\alpha$-[N-[3-phenyl-1-(R)-phosphonopropyl]-L-leucyl]-L-arginine (i)
N-[1-(R)-diethoxyphosphoryl-3-phenylpropyl]-L-leucine benzyl ester To a solution of 400 mg of diethyl 1-(R)-amino-3-phenylpropylphosphonate in 5 ml of anhydrous dichloromethane was added a solution of 0.25 ml of triethylamine and 627 mg of benzyl 2-(R)-trifluoromethanesulfonyloxy-4-methylpentanoate in 2.5 ml of anhydrous dichloromethane, and the mixture was stirred at room temperature overnight. The reaction mixture was diluted with 30 ml of dichloromethane, and the diluted solution was washed with 20 ml of water and dried over anhydrous magnesium sulfate. Then the solvent was distilled off under reduced pressure. The residue was purified by silica gel chromatography (hexane: ethyl acetate=1:1) to yield the title compound as a colorless oil (238 mg).

(ii)
N-[1-(R)-diethoxyphosphoryl-3-phenylpropyl]-L-leucine

To a solution of 230 mg of N-[1-(R)-diethoxyphosphoryl-3-phenylpropyl]-L-leucine benzyl ester in 5 ml of 95% ethanol was added 50 mg of 10% Pd—C, and the mixture was stirred under an atmospheric pressure of hydrogen at room temperature for 3 hours. The Pd—C was filtered off, and the solvent was distilled off under reduced pressure to yield the title compound as a colorless oil (190 mg).

(iii)
N$^\alpha$-[N-[1-(R)-diethoxyphosphoryl]-3-phenylpropyl-L-leucyl]-N$^\omega$-nitro-L-arginine benzyl ester A solution of 73 mg of N-[1-(R)-diethoxyphosphoryl-3-phenylpropyl]-L-leucine and 149 mg of N$^\omega$-nitro-L-arginine benzyl ester di-p-toluenesulfonate in 5 ml of dichloromethane was cooled to 0° C. Then 65 μl of triethylamine, 53 mg of 1-hydroxybenzotriazole monohydrate and 66 mg of 1-ethyl-3-(3-dimethylaminopropyl)-carbodiimide hydrochloride were added to the solution. The mixture was then stirred at room temperature for 3 hours and diluted with 30 ml of ethyl acetate. The diluted solution was washed with a saturated aqueous solution of sodium bicarbonate, 1N hydrochloric acid and brine, and then dried over anhydrous magnesium sulfate. Then the solvent was distilled off under reduced pressure and the residue was purified by silica gel chromatography (ethyl acetate) to yield the title compound as a colorless oil (87 mg).

(iv)
N$^\omega$-nitro-N$^\alpha$-[N-[3-phenyl-1-(R)-phosphonopropyl]-L-leucine]-L-arginine N$^\alpha$-[N-[1-(R)-diethoxyphosphoryl]-3-phenylpropyl-L-leucyl]-N$^\omega$-nitro-L-arginine benzyl ester (58 mg) was dissolved in 0.5 ml of a 30% solution of hydrogen bromide in acetic acid, and the resulting solution was stirred at room temperature over night. The reaction mixture was concentrated under reduced pressure, and 5 ml of a 0.1% aqueous solution of trifluoroacetic acid was added to the residue. The resulting solution was passed through a Sep Pak C18$^{TM}$ cartridge and the cartridge was washed with 25 ml of water. The desired product was eluted with 25 ml of acetonitrile, and the solvent was distilled off under reduced pressure to yield the title compound as a colorless powder (30 mg).

High resolution FAB-MS (m/e, as $C_{21}H_{35}N_6O_8P+H)^+$): Calculated: 531.2332 Found: 531.2361

$^1$H-NMR (300 MHz, DMSO, δ ppm): 0.88(3H,d,J=6.4 Hz), 0.91(3H,d,J=6.4 Hz), 1.35-2.00(7H,m), 2.00-4.45(9H,m), 7.05-7.33(5H,m), 7.72-9.00(3H,m)

EXAMPLE 15

Preparation of a transfusion solution for drip infusion

Isomer B obtained in Example 1 (1 g) was dissolved in 500 ml of a 5% glucose solution for transfusion. The resulting solution was filtered through a Millipore filter (pore size: 0.22 μm) under aseptic conditions. A transfusion vial was filled with the filtrate to afford a transfusion solution for drip infusion.

EXAMPLE 16

Preparation of a solution for intravenous injection

Isomer B obtained in Example 1 (1 g) was dissolved in 100 ml of physiological saline. The resulting solution was filtered through a Millipore filter (pore size: 0.22 μm) under aseptic conditions to afford a solution for intravenous injection.

EXAMPLE 17

Preparation of tablets
Isomer B of Example 1 7 parts
a 60% aq. ethanol solution 5 parts
Hydroxypropylcellulose 1 part
Lactose 10.9 parts
Corn starch 1 part
Magnesium stearate 0.1 parts Five parts of a 60% aqueous ethanol solution containing 1 part of hydroxypropylcellulose was prepared, and then kneaded with 7 parts of Isomer B of Example 1, 10.9 parts of lactose and 1 part of corn starch. The mixture was dried under reduced pressure, mixed with 0.1 parts of magnesium stearate, and compressed by a conventional method into tablets.

REFERENTIAL EXAMPLE 1

Production of diethyl
1-(R)-amino-3-phenylpropylphosphorate

The title compound was produced by phenethylation and the successive hydrolysis of diethyl (1S, 4R)-[(1, 7, 7-trimethylbicyclo[2.2.1]hepto-2-ylidenamino)methyl]-phosphonate in the same manner as Ulrich Schollkopf and Rainer Schutze's (Liebigs Ann. Chem., p. 45–49, 1987).

$^1$H-NMR (90 MHz, CDCl$_3$, δ ppm): 1.32(6H,dt,J=1.1 Hz,7.0 Hz), 1.20–2.30(4H,m), 2.50–3.16(3H,m), 4.12(4H,dq,J=7.0 Hz,7.8 Hz), 7.03–7.54(5H,m)

FAB-MS (m/e): 272 (M+H)+

Rotation: [α$^{20}$$_D$]= −17.30° (0.97% in chloroform)

REFERENTIAL EXAMPLE 2

Production of benzyl
2-(R)-trifluoromethanesulfonyloxy-4-methylpentanoate (i) 2-(R)-hydroxy-4-methylpentanoic acid To a solution of 2.62 g of D-leucine in 30 ml of 1N sulfuric acid at 0° C. was added a solution of sodium nitrite (2.07 g) in water (15 ml). The resulting solution was stirred at 0° C. for 3 hours, and then at room temperature for 2 hours. The reaction mixture was extracted with ethyl ether (10 ml×3), and the combined organic layers were washed with brine, and then dried over anhydrous magnesium sulfate. The solvent was distilled off under reduced pressure to yield the title compound as a light-yellow solid (2.08 g).

(ii) Benzyl 2-(R)-hydroxy-4-methyl-pentanoate

A mixture of 2.05 g of 2-(R)-hydroxy-4-methylpentanoic acid, 2.01 g of benzyl alcohol and 0.251 g of p-toluenesulfonic acid monohydrate in 40 ml of benzene was heated to reflux for 1.5 hours. The reaction mixture, after being allowed to cool, was washed with a saturated aqueous solution of sodium bicarbonate and brine, and then dried over anhydrous magnesium sulfate. Then the solvent was distilled off under reduced pressure to yield the title compound as a colorless oil (2.30 g).

(iii) Benzyl
2-(R)-trifluoromethanesulfonyloxy-4-methylpentanoate

Benzyl 2-(R)-hydroxy-4-methylpentanoate (2.22 g) was dissolved in 10 ml of anhydrous dichloromethane, and then the solution was cooled to 0° C. Pyridine (1.05 ml) was added to the solution, and 2.46 ml of trifluoromethanesulfonic anhydride was added dropwise to the mixture over 15 minutes. The mixture was then stirred at 0° C. for 15 minutes. The resulting precipitate was filtered off, and the filtrate was concentrated under reduced pressure. The residue was purified by silica gel chromatography (dichloromethane) to yield the title compound as a colorless oil (2.79 g).

$^1$H-NMR (90 MHz, CDCl$_3$, δ ppm): 0.95(6H,d,J=5.7 Hz), 1.55–2.10(3H,m), 5.05–5.30(1H,m), 5.25(2H,s), 7.37(5H,s)

TEST EXAMPLES

In the following section will be described the endothelin-converting enzyme (ECE) inhibitory activities of aminophosphonic acid derivatives of the present invention.

ECE Activity Inhibition Test

ECE was prepared according to the method already published by Yano, et.al. (Biochem. Biophys. Res. Commun., Vol. 171, p.1192–1198, 1990), and 11 μg of ECE and 1 μM of big endothelin-1 were reacted with a 0.5M Tris-HCl buffer solution (pH 7.2) at 37° C. for 90 minutes in the presence or absence of a test compound, after which the amount of endothelin-1 produced thereby was determined by the RIA method, and the ECE inhibition activity of the test compound was evaluated. Table 1 shows that the compounds of the present invention exhibit a very potent ECE inhibition.

TABLE 1

| ECE INHIBITION BY 10 μM OF THE TEST COMPOUND | |
|---|---|
| Test compound | Inhibition (%) |
| Compound of Example 1 (Isomer B) | 88 |
| Compound of Example 2 (Isomer B) | 90 |
| Compound of Example 3 (Isomer B) | 81 |
| Compound of Example 4 (Isomer B) | 72 |
| Compound of Example 6 | 80 |
| Compound of Example 9 (Isomer B) | 71 |
| Compound of Example 10 (Isomer B) | 76 |
| Compound of Example 11 | 84 |
| Phosphoramidon (control) | 64 |

Effect on Big Endothelin-1-induced Contraction in Isolated Pig Coronary Arteries Pig coronary arteries were isolated, and a spiral preparation having a width of 1 mm and a length of 10 mm was prepared therefrom. These samples were then placed in a 5 ml Magnus' tube filled with Krebs-Henseleit solution saturated with a gas mixture of 95% $O_2$ and 5% $CO_2$, and a change in the tension was isometrically measured and recorded.

The influence of a representative compound of the present invention (Compound of Example 11) to the increase in the tension produced by 30 nM of big endothelin-1 was examined. The test compound was added to the Magnus' tube 40 minutes prior to the addition of big endothelin-1.

A 100% increase in the tension was defined as that in the case of no addition of the test compound (control) at 2 hours after addition of big endothelin-1, and the comparison with the increase in the tension in the cases where the test compound was added is shown in Table 2. The compound of Example 11 exhibited a dose-dependent inhibition, and the $IC_{50}$ value was calculated to be 16 μM. In addition, the test compound exhibited no effect on the increase in the tension caused by 0.3 nM of endothelin-1. Further, the compound itself exhibited no effect on the tension of the above mentioned blood vessel samples. Thus, as shown above, the compound of the present invention exhibited a specific and considerable inhibition against endothelin-induced contraction caused by the conversion of big endothelin-1 to endothelin-1.

TABLE 2

INHIBITION ACTIVITY OF COMPOUND OF EXAMPLE 11 AGAINST BIG ENDOTHELIN-1-INDUCED CONTRACTION IN ISOLATED PIG CORONARY ARTERIES

| Dose (μM) | Contraction (% of control) |
| --- | --- |
| 10 | 59.9 |
| 30 | 35.3 |
| 100 | 2.7 |

Effect on Big Endothelin-1-induced Contraction in Isolated Guinea Pig Bronchial Smooth Muscles Bronchia (outer diameter approximately 2 mm) were isolated from the lung of a guinea pig, and the connective tissue, lung parenchymal tissue, etc. were peeled off, and then a ring preparation (4 mm in length) was prepared. These samples were placed in a 5 ml Magnus' tube filled with Krebs-Henseleit solution saturated with a gas mixture of 95% $O_2$ and 5% $CO_2$, and a change in tension was isometrically measured and recorded.

The influence of a representative compound of the present invention (Compound of Example 2, Isomer B) to the increase in the tension produced by 100 nM of big endothelin-1 was examined. The test compound was added into the Magnus' tube 40 minutes prior to the addition of big endothelin-1.

A 100% increase in the tension was defined as that in the case of no addition of the test compound (control) at 2 hours after addition of big endothelin-1, and the comparison with the increase in the tension in the cases where the test compound was added is shown in Table 3. The compound of Example 2 (Isomer B) exhibited a dose-dependent inhibition, and the $IC_{50}$ value was calculated to be 16 μM. In addition, the test compound itself exhibited no effect on the tension of the above mentioned bronchial samples. Thus, as shown above, the compound of the present invention exhibited a specific and considerable inhibition against bronchial contraction induced by the addition of big endothelin-1 in the above mentioned bronchial samples.

TABLE 3

INHIBITION ACTIVITY OF COMPOUND OF EXAMPLE 2 (ISOMER B) AGAINST BIG ENDOTHELIN-1-INDUCED CONTRACTION IN ISOLATED GUINEA PIG BRONCHIA

| Dose (μm) | Contraction (% of control) |
| --- | --- |
| 1 | 105 |
| 10 | 54.9 |
| 100 | 32.9 |

Effect on Big Endothelin-1-induced Increase in Airway Resistance in Guinea Pigs Guinea pigs were first anesthetized with urethane, and then the necks were subjected to median incision, a tracheal cannula was inserted in the trachea. Spontaneous respiration was interrupted with succinylcholine (5 mg/kg, hypodermic injection), and then an artificial respirator was used to effect artificial ventilation (10 ml/air/kg, 6 strokes/min). The airway pressure was then measured and recorded using the Konzett and Rössler method (Arch. Exp. Path. Pharmacol., Vol. 135, p.71-74, 1940), via an airway contraction transducer from the tracheal cannula.

Examined was the influence of a representative compound of the present invention (Compound of Example 1, Isomer B) to the increase in airway pressure produced by the administration of 5 nmol/kg of big endothelin-1 through a polyethylene tube inserted into the common carotid vein. The test compound was injected into the common carotid vein 5 minutes before the administration of big endothelin-1. Also, upon completion of the experiment, the change in airway pressure obtained by blockage of the trachea was defined as a 100% increase in airway pressure, and the measured increases in airway pressure were expressed as percentages of this value.

Figure 1:
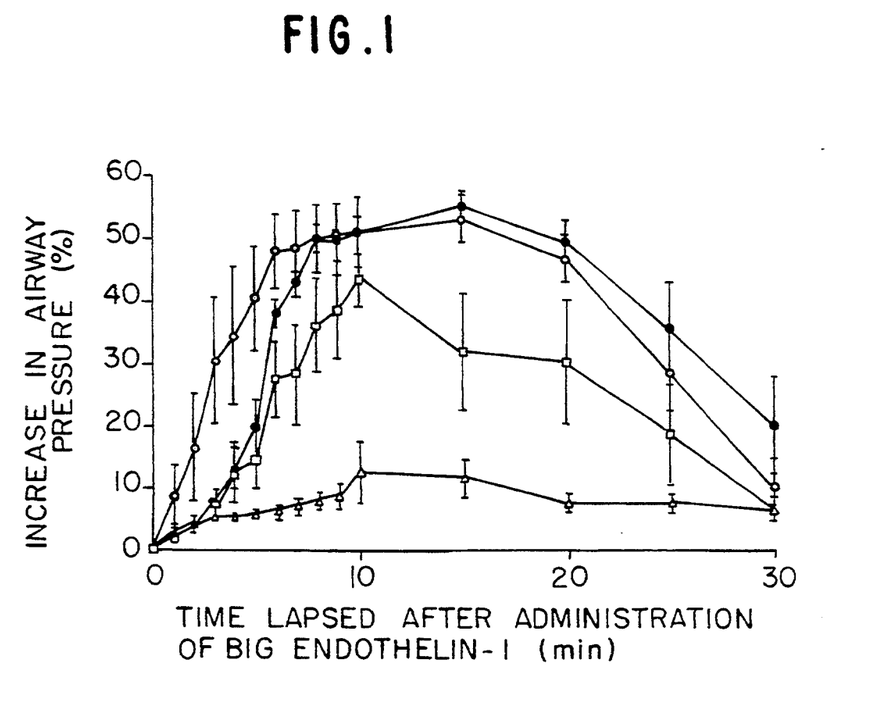
FIG. 1 shows the result that the compound of Example 1 (Isomer B) remarkably inhibits the increase in the airway pressure induced by big endothelin in guinea pigs. In the figure, a symbol ○ stands for the control (group to which only saline of the vehicle for the test compounds was administered) and symbols, ●, □ and △ stand for the groups to which 0.3 mg/kg, 1.0 mg/kg and 3.0 mg/kg of the test compound were administered, respectively. Each symbol represents an average of measured values for five guinea pigs of each group, while each vertical line with a symbol represents a standard deviation range.

The effects are shown in FIG. 1. In the figure, a symbol ○ stands for the control group (group to which only saline of the vehicle for the test compound was administered), and symbols ●, □ and △ stand for the groups to which 0.3 mg/kg, 1.0 mg/kg and 3.0 mg/kg of the test compound were administered respectively. Each symbol represents an average of measured values for five guinea pigs of each group, while each vertical line for a symbol represents a standard deviation range.

AS shown in FIG. 1, in the control group, the administration of big endothelin-1 caused a gradual increase in airway pressure, reaching a peak after 15 minutes. The airway pressure then began to decrease slowly, but an increase therein could be observed even up to 30 minutes after the administration. On the other hand, the compound of Example 1 (Isomer B) suppressed the increase in airway pressure induced by big endothelin-1, in a dose-dependent manner (0.3-3.0 mg/kg). On the other hand, an administration of the test compound alone resulted in no change in the airway pressure. Thus, as described above in this animal experiment, the compound of the present invention exhibited a specific and considerable inhibition against the increase in airway resistance induced by big endothelin-1.

While the invention has been described in detail and with reference to specific embodiments thereof, it will be apparent to one skilled in the art that various changes and modifications can be made therein without departing from the spirit and scope thereof.

What is claimed is:

1. An aminophosphonic acid derivative of formula [I]:

wherein n is an integer 2 or 3; $R^1$ represents a phenyl, naphthyl, indolyl, benzothienyl, benzofuryl or benzoxazolyl group which is unsubstituted or substituted with 1 to 3 substituents selected from the group consisting of hydroxyl and lower alkyloxy groups, or a hydrogen atom; $R^2$ represents a lower alkyl group, a benzyl group, a 4-hydroxybenzyl group, a 3-indolylmethyl group or a β-phenethyl group; and A represents an amino acid selected from the group consisting of tryptophan, tyrosine, phenylalanine, homophenylalanine, α-naphthylalanine and $N^\omega$-nitroarginine, or a pharmaceutically acceptable salt thereof.

2. A pharmaceutical composition comprising a therapeutically effective amount of the compound of formula [I] as recited in claim 1, or a pharmaceutically acceptable salt thereof, and a pharmaceutically acceptable carrier.

3. A method of treating a condition in a mammal, the treatment of which is effected or facilitated by a decrease in endothelin mediated actions, comprising the administration, in an amount that is effective for antagonizing the effect of endothelin, of the compound of formula [I] as recited in claim 1.

4. The method as claimed in claim 3, wherein the condition is a disorder related to endothelin.

5. The method as claimed in claim 4, wherein the disorder is selected from the group consisting of hypertension, pulmonary hypertension, Raynaud's disease, Buerger's disease, Takayasu's disease, Kawasaki's disease, diabetes, bronchial asthma, arteriosclerosis, acute renal failure, myocardial infarction, angina pectoris, cerebral vasospasm, cerebral infarction, endotoxin shock, endotoxin-induced multiple organ failure or disseminated intravascular coagualation, cyclosporin- or cisplatin-induced renal failure or hypertension, congestive heart failure, vascular restenosis, and inflammatory bowel diseases.

6. The method as claimed in claim 3, wherein the mammal is human.

* * * * *